United States Patent
Kacker et al.

(10) Patent No.: US 7,498,390 B2
(45) Date of Patent: Mar. 3, 2009

(54) CHROMIUM COMPLEXES AND THEIR USE IN OLEFIN POLYMERIZATION

(75) Inventors: Smita Kacker, Houston, TX (US); Enock Berluche, Phillipsburg, NJ (US); Robert T. Stibrany, Long Valley, NJ (US); Joseph A. Sissano, Leonardo, NJ (US); Lisa S. Baugh, Ringoes, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 20 days.

(21) Appl. No.: 11/904,057

(22) Filed: Sep. 25, 2007

(65) Prior Publication Data
US 2008/0021181 A1 Jan. 24, 2008

Related U.S. Application Data

(62) Division of application No. 11/152,802, filed on Jun. 14, 2005, now Pat. No. 7,297,805.

(60) Provisional application No. 60/583,881, filed on Jun. 29, 2004.

(51) Int. Cl.
*C08F 4/69* (2006.01)
(52) U.S. Cl. .................. 526/161; 502/103; 502/167; 526/131; 526/133; 526/165
(58) Field of Classification Search .......... 502/103, 502/167; 526/131, 133, 161, 165
See application file for complete search history.

(56) References Cited

FOREIGN PATENT DOCUMENTS
WO  WO 2004/083263  * 9/2004

* cited by examiner

*Primary Examiner*—Caixia Lu
(74) *Attorney, Agent, or Firm*—Robert A. Migliorini

(57) ABSTRACT

A composition having the formula I

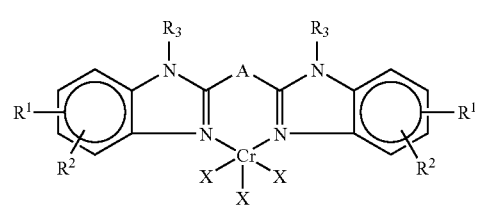

where $R^1$ and $R^2$ are independently hydrogen, $C_1$ to $C_{12}$ linear and branched alkyl, $C_3$ to $C_{12}$ cycloalkyl, aryl, $C_1$ to $C_{12}$ alkoxy, F, Cl, $SO_3$, $C_1$ to $C_{12}$ perfluoroalkyl, and $N(CH_3)_2$,
$R^3$ is independently selected from the group consisting of hydrogen, $C_1$ to $C_{12}$ linear and branched alkyl, $C_3$ to $C_{12}$ cycloalkyl, aryl, and 2,2,2-trifluoroethyl,
A is —$C(R^4)$—, —$(CH_2)_x$—, —$(CH_2)_xNH(CH_2)_x$—, or —$CY_2CY_2$—, ps where $R^4$ is a hydrocarbyl, halosubstituted hydrocarbyl, or alkoxy group of from 1 to 12 carbon atoms, x is an integer from 1 to 12, and Y is halogen,
and
X is halogen, triflate, acetate, trifluoroacetate, hydride, or tetrafluoroborate.
When combined with an activating co-catalyst is useful in polymerizing olefinic monomers.

8 Claims, No Drawings

CHROMIUM COMPLEXES AND THEIR USE IN OLEFIN POLYMERIZATION

This application is a divisional application filed under 37 C.F.R. 1.53(b) of parent application serial number U.S. Ser. No. 11/152,802 filed Jun. 14, 2005 now U.S. Pat. No. 7,297,805, the entirety of which is hereby incorporated herein by reference, which claims the benefit of U.S. Provisional application 60/583,881 filed Jun. 29, 2004.

FIELD OF INVENTION

The present invention is directed toward chromium complexes and their use in olefin polymerization. More specifically the invention is directed toward chromium trihalide complexes having bis-benzimidazole ligands and their use in olefin polymerization.

BACKGROUND OF INVENTION

Nitrogen-based chelates of transition metals such as Ti, Ni, Pd, Co and Fe have been actively investigated in recent years as olefin polymerization catalysts. Those incorporating bidentate α-diimine and tridentate bisiminopyridine ligands have been found to be highly active catalysts for olefin polymerization.

More recently, similar investigations of coordination chemistry and catalysis have been extended to chromium (III) complexes containing certain imidizole-based chelate ligands. These complexes, when activated with methyl aluminoxane ("MAO") were found to catalyze the oligomerization of ethylene. (See Ruther et al, Organometallics, 2001, 20, 1247-1250).

Despite the advances made in catalyst systems employing chromium, there is a continuing need for new catalysts that will provide a greater degree of control over polymerization processes. Homogenous, chromium-based catalysts are believed to possess the potential of providing better control over polymerization processes than many other organometallic catalysts. For example, a neutral nickel (II) catalyst containing bidentate monoanionic ligands produce linear α-olefins with a very wide range Schulz-Flory type distribution. An object of the present invention, therefore, is to provide novel chromium based catalysts useful in the polymerization of olefins.

SUMMARY OF INVENTION

In one embodiment the invention is a composition having the formula

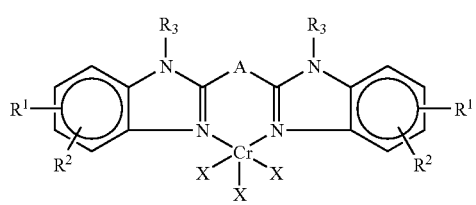

I where $R^1$ and $R^2$ are independently hydrogen, $C_1$ to $C_{12}$ linear and branched alkyl, $C_3$ to $C_{12}$ cycloalkyl, aryl, $C_1$ to $C_{12}$ alkoxy, F, Cl, $SO_3$, $C_1$ to $C_{12}$ perfluoroalkyl, and $N(CH_3)_2$, $R^3$ is independently selected from the group consisting of hydrogen, $C_1$ to $C_{12}$ linear and branched alkyl, $C_3$ to $C_{12}$ cycloalkyl, aryl, and 2,2,2-trifluoroethyl, A is —C($R^4$)—, —$(CH_2)_x$—, —$(CH_2)_xNH(CH_2)_x$—, or —$CY_2CY_2$—, where $R^4$ is a hydrocarbyl, halosubstituted hydrocarbyl, or alkoxy group of from 1 to 12 carbon atoms, x is an integer from 1 to 12, and Y is halogen, and X is halogen, triflate, acetate, trifluoroacetate, hydride, or tetrafluoroborate.

In another embodiment the invention is a catalyst comprising the reaction product of a compound of formula I and an activating co-catalyst.

In yet another embodiment a method for making polyolefins is provided which includes contacting olefinic monomers under polymerization conditions with a catalyst composition comprising a composition having formula I and an activating co-catalyst.

These and other features, aspects and advantages of the present invention will become better understood with regard to the following description and appended claims.

DETAILED DESCRIPTION

The invention provides novel chromium bis-benzimidazole complexes which, when used with an activating co-catalyst, provides a novel catalyst composition.

The chromium complexes of the invention are represented by the formula

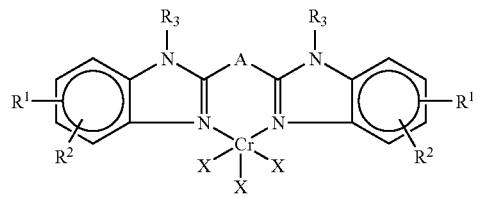

I where $R^1$ and $R^2$ are independently, hydrogen, $C_1$ to $C_{12}$ linear and branched alkyl, $C_3$ to $C_{12}$ cycloalkyl, and aryl, $C_1$ to $C_{12}$ alkoxy, F, Cl, $SO_3$, $C_1$ to $C_{12}$ perfluoroalkyl, and $N(CH_3)_2$, $R^3$ is independently selected from the group consisting of hydrogen, $C_1$ to $C_{12}$ linear and branched alkyl, $C_3$ to $C_{12}$ cycloalkyl, aryl, and 2,2,2-trifluoroethyl, A is —C($R^4$)—, —$(CH_2)_x$—, —$(CH_2)_xNH(CH_2)_x$—, or —$CY_2CY_2$—, where $R^4$ is a hydrocarbyl, halosubstituted hydrocarbyl, or alkoxy group of from 1 to 12 carbon atoms, x is an integer from 1 to 12, and Y is halogen, and X is halogen, triflate, acetate, trifluoroacetate, hydride, or tetrafluoroborate.

Preferred compositions are those in which $R^3$ is an alkyl group, especially n-butyl; where $R^1$ and $R^2$ are hydrogen or methyl; where A is —C($C_4H_9$)—, or —$CF_2CF_2$—; and X is chlorine.

The compounds of the invention are made by reacting Cr(III) halide, e.g., $CrCl_3$ or $CrCl_3$—$(THF)_3$ (THF=tetrahydrofuran), with the appropriate ligand. This is done by adding the chromium compound to a solvent or diluent and then adding the ligand to the solvent or diluent. Suitable solvents or diluents include liquid or supercritical gases such as $CO_2$, tetrahydrofuran, straight and branched alkanes like isobutane, butane, pentane, hexane and mixtures thereof; cyclic and alicyclic hydrocarbons like cyclohexane, methylcyclohexane; halogenated hydrocarbons such as chlorobenzene; perfluorinated $C_{4-10}$ alkanes; and aromatic hydrocarbons like toluene. The resulting chromium complex is separated by removal of, or precipitation from, the diluent or solvent.

Optionally, the chromium complex may be prepared in the solvent or diluent to be used for the polymerization. In this instance, the chromium complex and the co-catalyst are typically combined in the solvent or diluent used for the polymerization immediately before adding the olefinic monomer to be polymerized.

As indicated the following ligands are preferred: 1,1'-bis (1-butylbenzimidazol-2-yl)pentane; 1,2-bis(1-butylbenzimidazol-2-yl)-1,1,2,2-tetrafluoroethane; and 1,1'-bis(1-butyl-4-methylbenzimidazol-2-yl)pentane.

1,1'-Bis(1-butylbenzimidazol-2-yl)pentane has the structure II:

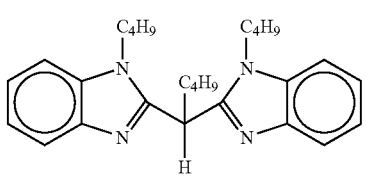

1,2-Bis(1-butylbenzimidazol-2-yl)-1,1,2,2 tetrafluoroethane has the structure III:

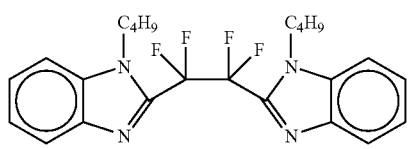

1,1'-Bis(1-butyl-4 methyl benzimidazol-2-yl)pentane has the structure IV:

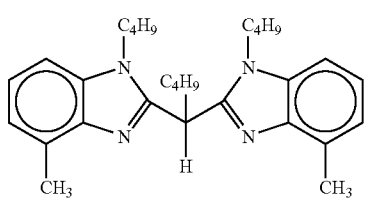

The ligands of the invention may be synthesized using techniques known to those skilled in the art. In this regard, see for example, U.S. Pat. No. 6,037,297, herein incorporated by reference.

The chromium compositions of the invention are combined with an activating co-catalyst to provide a catalyst useful in polymerizing olefins. Examples of such co-catalysts include aluminum compounds containing an Al—O bond such as the alkylalumoxanes, of which methyl alumoxane ("MAO") is an example. Other suitable co-catalysts include mixtures of alkyl alumoxane with one or more trialkyl aluminum or trialkyl boron compounds, and mixtures of alkyl alumoxanes with aluminum halides or boron halides and an alkylating agent. Examples of alkylating agents include methyl magnesium chloride and methyl lithium. Typically the alkyl group will range from 1 to about 12 carbon atoms.

A preferred activating co-catalyst is methylalumoxane.

Olefinic monomers that are useful in forming polymers with the catalyst of the invention include, for example, ethylenically unsaturated monomers, non-conjugated dienes, oligomers and higher molecular weight, vinyl terminated macromers. Representative examples include $C_{2-20}$ olefins, vinylcyclohexane, tetrafluoroethylene, and mixtures thereof. Preferred are $C_{2-10}$ α-olefins such as ethylene and 1-hexene.

In general the polymerization is accomplished at temperatures ranging from about −100° C. to 250° C., preferably 0° C. to 250° C., and pressures of from atmospheric to 2000 atmospheres (200 Mpa). Suitable polymerization conditions include those known to be useful for olefin polymerization catalysts when activated by aluminum or boron compounds. Suspension, solution, slurry, gas phase or other process conditions may be employed if desired.

The polymerization typically will be conducted in the presence of a solvent. Suitable solvents include toluene, methylene chloride, chlorobenzene, THF, and the like.

The polymerization will be conducted for a time sufficient to form the polymer and the polymer is recovered by techniques known in the art and illustrated in the examples hereinafter.

In the following examples involving ligands and catalysts, stage melting points were determined visually and are uncorrected. DSC melting points were taken with a TA Instruments 2920 calorimeter using a scan rate of 10° C./minute. Elemental analyses were carried out by QTI, Whitehouse, N.J. Field desorption mass spectra were obtained on a VG-ZAB system. Infrared spectra were obtained on a Mattson Galaxy Series 5000 spectrometer running First software. NMR spectra were obtained using a Bruker Avance 400 Ultrashield spectrometer, with default calibration to $CFCl_3$ used as a standard for $^{19}F$ spectra. Solid-state NMR experiments were carried out using a Chemagnetics CMXII-200 spectrometer.

EXAMPLE 1

Synthesis of
1,1'-bis(1-butylbenzimidazol-2-yl)pentane
(TriBu-BBIM)

In a 250 mL 35/25 ball joint flask, 1,2-phenylenediamine (54 mmol) was combined with malonic acid (2 equivalents). Polyphosphoric acid (~100 g) was added directly to the solid mixture. The flask was fitted with an air-driven mechanical stirring shaft and heated to 160° C. under a nitrogen purge maintained with a septum and needle. The molten mixture was stirred for 7 hours and subsequently poured slowly into a large (1 L) excess of cold water. A Waring™ blender was used to grind the solid product/water slurry. The water was then neutralized to a pH of ~8 with ammonium hydroxide. The product, 1,1'-bis(1-butylbenzimidazol-2-yl)pentane, was isolated by filtration and dried in a vacuum oven at 110° C. for several days. A 23.00 g (0.093 mol) quantity of this product was placed in a 300 mL round bottom flask with a side arm. This was followed by the addition of 25 mL of anhydrous DMSO. The flask was then fitted with a bubbler. Under a flow of nitrogen, 6.0 g of sodium hydride (60% dispersion in mineral oil) was added over one hour while stirring at 0° C. The reaction was allowed to warm to room temperature, and 25.00 mL (0.220 mol) of 1-iodobutane was added dropwise over one hour. The reaction mixture was left stirring under nitrogen for 48 hours. The reaction mixture was quenched with water and then an additional 400 mL of water was added. After stirring for one half hour, a biphasic solution was obtained. The organic layer was extracted with cyclohexane and was washed with water. The volatiles were removed from the cyclohexane phase under reduced pressure to leave a dark oil. The oil was chromatographed on silica gel with methylene chloride as the eluent. The solvent was removed under reduced pressure from the combined eluents to give a very pale-pink oil that crystallized upon standing at room temperature ($C_{27}H_{36}N_4$, FW=416.61). Yield: 20.44 g (67%). $^1$H NMR (CDCl$_3$): δ 7.79 (m, 2H), 7.24 (m, 6H), 4.88 (t, J=7.9 Hz, 1H), 4.16 (d sp, J=5.0 Hz, J=40.9 Hz, 4H), 2.59 (m, 2H), 1.44 (m, 4H), 1.16 (m, 4H), 1.10 (m, 2H), 0.99 (m, 2H), 0.89 (t, J=6.8 Hz, 3H), 0.61 (t, J=7.0 Hz, 6H). $^{13}$C NMR (CDCl$_3$): δ 151.8, 142.4, 135.6, 122.6, 122.0, 119.6, 109.7, 44.0, 40.9, 31.5, 31.2, 30.1, 22.5, 20.0, 14.0, 13.4. IR (KBr pellet, cm$^{-1}$): 3050 (m), 2955 (m), 2931 (m), 2862 (m), 1613 (w), 1501 (m), 1458 (s), 1400 (s), 1331 (m), 1285 (m), 1008 (m), 933 (m), 743 (s), 434 (w). $R_f$=0.73 (ethyl acetate). FD-MS m/z (%): 416.1 (M$^+$). Melting point (stage) 82-83° C.

EXAMPLE 2

Synthesis of [1,1'-bis(1-butylbenzimidazol-2-yl)pentane]CrCl$_3$ ((TriBu-BBIM)CrCl$_3$) (A)

CrCl$_3$·(THF)$_3$ (0.27 g, 0.72 mmol) was weighed into a flask equipped with a stirrer under argon. THF (15 mL) was added to the flask followed by the ligand triBu-BBIM (0.33 g, 0.79 mmol). The solution was stirred overnight at room temperature. At the end of this time period, the solution was added to 100 mL of diethyl ether. The precipitate was filtered and washed with ether and hexane and dried under vacuum at room temperature.

Yield: 0.4 g, 87% ($C_{27}H_{36}N_4CrCl_3$, FW=574.96). NMR spectra in CDCl$_3$ and THF showed broad peaks, indicating a paramagnetic center. IR (KBr pellet, cm$^{-1}$): 2959.0 (s), 2872.2 (m), 1614.5 (m), 1597.2 (w), 1494.9 (s), 1479.5 (s), 1460.2 (s), 1435.1 (m), 1375.3 (w), 1338.7 (w), 1275.0 (m), 750.3 (s). Melting point (stage) 215° C.

EXAMPLE 3

Synthesis of 1,2-bis(1-butylbenzimidazol-2-yl)-1,1,2,2-tetrafluoroethane (DiBu-(C$_2$F$_4$)-BBIM)

In a 250 mL 35/25 ball joint flask, 1,2-phenylenediamine (5.92 g, 54.7 mmol) was combined with tetrafluorosuccinic acid (5.2 g, 27.36 mmol). Polyphosphoric acid (83 g) was added directly to the solid mixture. The flask was fitted with an air-driven mechanical stirring shaft and heated to 160° C. under a nitrogen purge maintained with a septum and needle. The molten mixture was stirred for 7 hours and subsequently poured slowly into a large (1 L) excess of cold water. A Waring™ blender was used to grind the solid product/water slurry. The water was then neutralized to a pH of ~8 with ammonium hydroxide. The brown particulate product, 1,2-bis(benzimidazol-2-yl)-1,1,2,2-tetrafluoroethane, was isolated by filtration, dried in a vacuum oven, ground to a fine powder with a mortar and pestle, and once again slurried in ca. 1 L water which was then neutralized to pH 8 with ammonium hydroxide. The solid was again collected by filtration and dried under diffusion pump vacuum at 110° C. for several days (7.96 g, 87%; $C_{16}H_{10}F_4N_4$, FW=334.27). A small amount of water was still present by $^1$H NMR (br s, 3.35 ppm). $^1$H NMR (d$_6$-DMSO): δ 13.66 (br s, 2 H, N$\underline{H}$), 7.67 and 7.34 (each br s, 4 H, aryl C—$\underline{H}$. $^{13}$C{$^1$H} NMR (solid state): δ 142.2, 135.5 ($\underline{C}$—N), 124.2, 120.2, 114.4 (aryl) ($\underline{C}$=N and $\underline{C}$F$_2$ not observed). $^{19}$F NMR (d$_6$-DMSO, vs. CFCl$_3$): δ-110.61. IR (KBr pellet, cm$^{-1}$): 3063 (m), 3011 (m), 2947 (m), 2864 (s), 2749 (s), 2699 (sh), 2647 (s), 2546 (m), 2527 (m), 1942 (w), 1903 (w), 1778 (w), 1622 (m), 1591 (m), 1537 (w), 1492 (m), 1456 (s), 1441 (s), 1389 (m), 1317 (m), 1279 (m), 1231 (m), 1202 (m), 1161 (vs), 1140 (vs), 1030 (m), 1014 (m), 999 (m), 941 (m), 909 (m), 887 (m), 789 (w), 766 (m), 739 (s), 675 (w), 619 (m), 590 (m), 545 (m), 434 (m). Elemental analysis calculated for $C_{16}H_{10}F_4N_4$: C, 57.49; H, 3.02; F, 22.73; N, 16.76. Found: C, 56.74; H, 2.82; F, 21.95; N, 16.70. FD-MS m/z (%): 334 (M$^+$, 100), 167 ($C_8H_5F_2N_2$, 6). Melting point (DSC, maximum): 383° C.

Subsequently, 1,2-bis(benzimidazol-2-yl)-1,1,2,2-tetrafluoroethane (4.02 g, 12.03 mmol) was degassed on a vacuum line in a 250 mL round-bottomed flask and flushed with argon. Anhydrous, nitrogen-sparged DMSO (135 mnL) was cannulated into the flask, resulting in a purple solution. Separately, a 500 mL three-necked flask equipped with a stirbar, addition funnel, vacuum adapter, and a septum was assembled in the glove box. Sodium hydride (powder, 1.15 g, 48.10 mmol) was added, and the flask was placed under argon on a Schlenk line. Anhydrous DMSO (35 mL) was added via cannula to form a slurry. The bis-benzimidazole solution was then cannulated into the addition funnel and added dropwise to the sodium hydride slurry over a 30 minute period at 0° C., giving a cloudy black solution. The reaction mixture was warmed to room temperature over a 2 hour period and sparged iodobutane (8.86 g, 48.12 mmol) was added. The slurry was stirred overnight at room temperature and the resultant clear amber, viscous solution was poured into 300 mL of deionized water. The organic products were isolated by extraction with 3×200 mL of cyclohexane, followed by back-extraction of the combined organic layers with 1×200 mL deionized water. Removal of cyclohexane gave 4.725 g (88%) of the light tan product, 1,2-bis(1-butylbenzimidazol-2-yl)-1,1,2,2-tetrafluoroethane, which was recrystallized from methanol at −10° C. (3.795 g, 71%; $C_{24}H_{26}F_4N_4$, FW=446.48). $^1$H NMR (CDCl$_3$): δ 7.80 (d, J=8.1 Hz, 2 H), 7.44 (d, J=8.1 Hz, 2 H), 7.38 (tr, J=7.5 Hz, 2 H), 7.31 (tr, J=7.6 Hz, 2 H) (aryl), 4.39 (tr, J=7.8 Hz, 4 H, C$\underline{H}_2$N), 1.87 (5, J=7.8 Hz, 4 H, C$\underline{H}_2$CH$_2$N), 1.44 (6, J=7.5 Hz, 4 H, C$\underline{H}_2$CH$_3$), 0.96 (tr, J=7.36, 6 H, C$\underline{H}_3$). $^{13}$C{$^1$H} NMR (CDCl$_3$, assigned by DEPT): δ 141.63 (aryl $\underline{C}$—N), 140.89 (tr, J$_{CF}$=28.4 Hz, $\underline{C}$=N), 135.40 (aryl $\underline{C}$—N), 124.53 and 122.95 (aryl o- to $\underline{C}$—N), 121.11 (aryl m- to $\underline{C}$—N), 112.84 (tr of tr, J$_{CF}$=253.4 and 34.4 Hz, $\underline{C}$F$_2$), 110.39 (aryl m- to C—N), 45.27 ($\underline{C}_2$N), 32.07 ($\underline{C}$H$_2$CH$_2$N), 19.94 ($\underline{C}$H$_2$CH$_3$), 13.46 ($\underline{C}$H$_3$). $^{19}$F NMR (CDCl$_3$, vs. CFCl$_3$): δ-107.52. IR (KBr pellet, cm$^{-1}$): 3082 (w), 3055 (m), 3017 (m), 2965 (s), 2936 (s), 2874 (s), 2737 (w), 1939 (w), 1896 (w), 1861 (w), 1811 (w), 1771 (w), 1734 (w), 1682 (w), 1615 (m), 1588 (m), 1499 (s), 1487 (s), 1464 (sh), 1452 (vs), 1424 (s), 1373 (s), 1335 (s), 1283 (w), 1248 (s), 1227 (m), 1167 (vs), 1142 (vs), 1101 (vs), 1005 (m), 980 (w), 963 (w), 916 (s), 893 (s), 783 (m), 739 (vs), 669 (m), 598 (m), 548 (w), 440 (m). Elemental analysis calculated for $C_{24}H_{26}F_4N_4$: C, 64.56; H, 5.87; F, 17.02; N, 12.55. Found: C, 64.32; H, 5.77; F, 16.93; N, 12.46. Melting point (stage): 112° C. FD-MS m/z (%): 446 (M$^+$, 100).

EXAMPLE 4

Synthesis of [1,2-bis(1-butylbenzimidazol-2-yl)-1,1,2,2-tetrafluoroethane]CrCl$_3$ (DiBu-(C$_2$F$_4$)-BBIM)CrCl$_3$) (B)

THF (5 mL) was added to DiBu-(C$_2$F$_4$)-BBIM (0.381 g, 0.053 mmol) in an argon-flushed 250 mL round-bottomed flask. The ligand was only partially soluble resulting in a slurry. CrCl$_3$·(THF)$_3$ (0.32 g, 0.853 mmol) in THF (10 mL) was added to the slurry. The mixture was stirred overnight at room temperature. Subsequently, methylene chloride (5 mL) was added and the resulting purple solution was stirred for 2 days. All solvents were then removed under vacuum, and the solids were washed with diethylether and hexane and dried under vacuum at room temperature to give [1,2-bis(1-butyl-benzimidazol-2-yl)-1,1,2,2-tetrafluoroethane]CrCl$_3$ as a light purple solid (0.52 g, 60%, $C_{24}H_{26}F_4N_4CrCl_3$, FW=604.84).

IR (KBr pellet, cm$^{-1}$): 3010 (s), 2890 (s), 1599.1 (s) .1498.8 (s), 1487.2 (s), 1452.5 (s), 1425.5 (s), 1373.4 (s), 1334.8 (s), 1248.0 (s), 1226.8 (m), 1167.0 (s), 1141.9 (s), 1103.4 (s), 1045.5 (w), 1006.9 (m), 962.5 (w), 916.2 (w), 993.1 (w), 862.2 (s), 796.7 (w), 744.6 (s). Melting point (stage) 125° C.

EXAMPLE 5

Synthesis of 1,1-bis(1-butyl-4-methylbenzimidazol-2-yl)pentane (TriBu-4,4'-diMe-BBIM)

The ligand precursor bis(4-methyl-2-benzimidazolyl)methane was first prepared in a procedure analogous to that given for 1,2-bis(benzimidaz-2-yl)-1,1,2,2-tetrafluoroethane in Example 3. The reagents used were: 2,3-diaminotoluene (15.26 g, 0.125 moles), malonic acid (6.53 g, 0.063 moles), and polyphosphoric acid (40 g). Upon heating, the contents of the flask had the viscosity of milk and turned a deep bluish purple color. The compound bis(4-methyl-2-benzimidazolyl)methane was isolated as a purple blue solid (11.35 g, 66% yield, $C_{17}H_{16}N_4$, FW=276.32).

$^1$H NMR (d$_6$-DMSO): δ 7.30 (d, J=7.9 Hz, 2 H), 7.03 (tr, J=7.6, 2 H), 6.94 (d, J=7.2, 2 H) (aryl CH), 4.46 (s, 2 H, CH$_2$), 2.50 (s, theoretical 12 H, Me). $^1$H NMR (CDCl$_3$): δ 7.30 (d, J=8), 7.04 (t, J=8), 6.94 (d, J=8) (aryl), 4.48 (s, CH$_2$), 2.49 (s, Me). $^1$H NMR (d$_7$-DMF): 7.35 (d, J=8.0, 2 H), 7.05 (t, J=7.6, 2 H), 6.96 (d, J=7.0, 2 H) (aryl), 4.59 (br s, 2 H, CH$_2$), 2.51 (s, 6 H, Me). $^{13}$C{$^1$H} NMR (d$_6$-DMSO, assigned by DEPT): δ 149.73 (C—N), 138.39, 138.01 (br, aryl C=N), 124.50 (aryl C—Me), 121.93, 121.58, 111.98 (aryl C—H), 29.35 (CH$_2$), 16.80 (CH$_3$). $^{13}$C{$^1$H} NMR (CDCl$_3$): δ 150.1 (C=N), 138.7, 138.4 124.8, 121.9, 121.6 112.3 (aryl carbons), 29.7 (bridging CH$_2$), 17.1(CH$_3$ on phenyl rings). IR (KBr pellet, cm$^{-1}$): 3377 (s), 3169 (sh), 3022 (s), 2918 (s), 2857 (sh), 2745 (s), 2693 (sh), 1904 (w), 1829 (w), 1761 (w), 1620 (w), 1533 (m), 1439 (vs), 1418 (sh), 1319 (w), 1277 (m), 1231 (m), 1157 (w), 1078 (w), 1022 (w), 783 (m), 745 (s). Elemental analysis calculated for $C_{17}H_{16}N_4$: C, 73.89; H, 5.84; N, 20.27. Found: C, 69.57; H, 5.49; N, 19.28 (incomplete combustion; calculated C:H:N ratio 12.7:1.0:3.5; found C:H:N ratio 12.7:1.0:3.5). FD-MS m/z (%): 277 (M$^+$, 100); 291 (13%, assigned as impurity with backbone CH$_2$ oxidized to C=O). Melting point (stage): appears to decompose by darkening, 145-165° C. Melting point (DSC, maximum): 282° C. (broad).

Subsequently, bis(4-methyl-2-benzimidazolyl)methane (10.0 g, 36.2 mmol) was reacted with NaH (3.47 g, 145 mmol) and iodobutane (12.4 mL, 20.1 g, 109 mmol) in anhydrous DMSO following a procedure analogous to the procedure given for 1,2-bis(1-butylbenzimidaz-2-yl)-1,1,2,2-tetrafluoroethane in Example 3. Following extraction, the burgundy-black product mixture (14.04 g, 87%) was eluted in batches through a silica gel column using 90:10 CH$_2$Cl$_2$/ethyl acetate. The collected product (R$_f$~0.7) was not completely separable from impurities at R$_f$~0.25-0.30 and the solvent front, and was subsequently eluted through a large neutral alumina column (J. T. Baker Type IB; 41 mm ID; stationary phase height~40 cm) using CH$_2$Cl$_2$. Following elution of a yellow byproduct, the pure ligand was collected as a red oil (R$_f$~0.74, 6.00 g, 37%) and dried at 60 °C. under high vacuum (C$_{29}$H$_{40}$N$_4$, FW=444.65). $^1$H NMR (CDCl$_3$): δ 7.12-7.01 (m, 6H, aryl), 4.90 (t, J=7.8 Hz, 1 H, backbone CH), 4.16 (m, 4 H, butyl CH$_2$N), 2.68 (s, 6 H, aryl CH$_3$), 2.57 (br apparent q, J=7.7 Hz, 2 H, backbone butyl CH$_2$CH), 1.45-1.43 (m, 4 H), 1.20-1.15 (m, 4 H), 1.04-0.95 (br m, 4 H) (butyl CH$_2$), 0.90 (t, J=7.0 Hz, 3 H, backbone butyl CH$_3$), 0.61 (t, J=7.3 Hz, 6 H, N-butyl CH$_3$). $^{13}$C{$^1$H} NMR (CDCl$_3$, assigned by DEPT): γ 151.23 (C=N), 141.76 and 135.23 (aryl C—N), 129.58 (aryl C—Me), 122.23, 122.17, 107.10 (aryl), 44.01 (CH$_2$N), 40.96 (backbone CH), 31.47 (N-butyl CH$_2$), 31.12, 30.12, 22.65 (backbone butyl CH$_2$), 20.00 (N-butyl CH$_2$), 16.70 (aryl CH$_3$), 13.97 (backbone butyl CH$_3$), 13.33 (N-butyl CH$_3$. IR (thin film on NaCl, cm$^{-1}$): 3055 (w, 3027 (w), 2957 (vs), 2932 (vs), 2873 (m), 1733 (w), 1601 (w), 1502 (m), 1459 (s), 1431 (s), 1399 (s), 1379 (m), 1366 (m), 1335 (m), 1268 (m), 1241 (m), 1215 (w), 1152 (w), 1115 (w), 1075 (w), 1037 (w), 970 (w), 947 (w), 904 (w), 872 (w), 780 (m), 749 (s) cm$^{-1}$. Elemental analysis calculated for $C_{29}H_{40}N_4$: C, 78.33; H, 9.07; N, 12.60. Found: C, 78.14; H, 9.03; N, 12.44. FD-MS m/z (%): 444 (M$^+$, 100).

EXAMPLE 6

Synthesis of [1,1-bis(1-butyl-4-methylbenzimidazol-2-yl)pentane]CrCl$_3$ ((TriBu-4,4'-diMe-BBIM)CrCl$_3$) (C)

This material was prepared following a procedure analogous to example 4. The reagents used were TriBu-4,4'-diMe-BBIM (0.561 g, 1.26 mmol, soluble in THF) and CrCl$_3$·(THF)$_3$ (0.473 g, 1.26 mmol). [1,1-Bis(1-butyl-4-methylbenzimidazol-2-yl)pentane]CrCl$_3$ was isolated as a light purple solid (0.45 g, 95%, C$_{29}$H$_{40}$N$_4$CrCl$_3$, FW=603.01). IR (KBr pellet, cm$^{-1}$): 1602.9 (s), 1531.6 (w), 1489.1(m), 1456.3 (m), 1043.6 (m), 1010.8 (s), 920.1 (w), 862.2(s), 781.2 (w), 748.4 (w). Melting point (stage): 115° C.

EXAMPLE 7

Polymerizations 99.9% pure ethylene (Grade 4.5, 99.995%, BOC Gases) was used as received. Methyl aluminoxane (30 wt % solution in toluene) was used as received from Albemarle. Toluene used as a solvent was dried by passing through purification columns of copper catalyst to remove oxygen and alumina to remove moisture (Pangborn, A. B.; Giardello, M. A.; Grubbs, R. H.; Rosen, R. K.; Timmers, F. J. *Organometallics* 1996, 15, 1518-1520). The polymer products were characterized by $^1$H, and $^{13}$C NMR using a Varian INOVA 300 spectrometer with a 5 mm switchable broadband probe. Molecular weights were determined using a Waters Associates 150° C. High Temperature gel permeation chromatography chromatograph equipped with three Polymer Laboratories mixed bed Type B columns in 1,2,4-trichlorobenzene at 135° C., using a Waters DRI detector and a polyethylene calibration curve.

Polymerizations were run in a 300 mL Parr™ reactor fitted with a mechanical stirrer. Catalyst was weighed in a glass liner under argon in the glove box; then, 75 mL of solvent was added to the catalyst. The reactor was then sealed and brought out of the glove box and attached to the ethylene feed. The specified amount of methyl aluminoxane solution was added to the reactor after dissolving ethylene in the solution at atmospheric pressure. The pressure was then increased to that specified for the run and the temperature for the run was set. At the end of the reaction, excess ethylene was vented, and the reaction was quenched with methanol. After cooling, the polymer was isolated by precipitation into acidic methanol, followed by drying under vacuum. Conditions and results are summarized in Table 1.

TABLE 1

| Ex. No. | Catalyst | mmol catalyst | Cr:Al ratio | Solvent | Temp °C | Time, hr | $C_2H_4$, psig | Activity, Kg of Product/ mol of Cr | MW ($\times 10^3$), MWD[a] |
|---|---|---|---|---|---|---|---|---|---|
| 7-1 | A | 0.035 | 1:500 | Toluene | 50 | 24 | 500 | 40 | 151, 4.4 |
| 7-2 (1 g of 1-hexene added) | A | 0.035 | 1:300 | Toluene | 50 | 24 | 500 | 13 | 140, 8.5 |
| 7-3 | A | 0.035 | 1:300 | $CH_2Cl_2$ | 50 | 20 | 500 | 507 | 120, 6.6 |
| 7-4 | A | 0.017 | 1:260 | $C_6H_5Cl$ | 50 | 20 | 500 | 124 | 86, 8.1 |
| 7-5 | A | 0.017 | 1:260 | $C_6H_5Cl$ | 24 | 2 | 100 | 95 | 157, 24.7 |
| 7-6 | A | 0.017 | 1:260 | $CH_2Cl_2$ | 24 | 2 | 100 | 142 | 108, 25.6 |
| 7-7 | A | 0.017 | 1:260 | Toluene | 24 | 2 | 100 | 19 | 337, 57.7 (bimodal) |
| 7-8 | C | 0.017 | 1:260 | Toluene | 22 | 2 | 100 | 8 | |
| 7-9 | B | 0017 | 1:260 | Toluene | 25 | 2 | 100 | 2 | |

[a] Mw = weight-average molecular weight. MWD = Mw/Mn (Mn = number-average molecular weight)

What is claimed is:

1. A method for polymerizing olefinic monomers comprising contacting an olefinic monomer or monomers under polymerization conditions with a catalyst composition comprising the reaction product of:

(a) a compound represented by the formula:

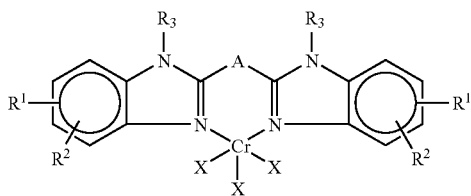

I and (b) an activating co-catalyst;

where $R^1$ and $R^2$ are independently hydrogen, $C_1$ to $C_{12}$ linear and branched alkyl, $C_3$ to $C_{12}$ cycloalkyl, aryl, $C_1$ to $C_{12}$ alkoxy, F, Cl, $SO_3$, $C_1$ to $C_{12}$ perfluoroalkyl, and $N(CH_3)_2$, $R^3$ is independently selected from the group consisting of hydrogen, $C_1$ to $C_{12}$ linear or branched alkyl, $C_3$ to $C_{12}$ cycloalkyl, aryl, and 2,2,2-trifluoroethyl, A is —CH($R^4$)—, —($CH_2$)$_x$—, or —$CY_2CY_2$—, where $R^4$ is a hydrocarbyl, halosubstituted hydrocarbyl, or alkoxy group of from 1 to 12 carbon atoms, x is an integer from 1 to 12, and Y is halogen, and X is halogen, triflate, acetate, trifluoroacetate, hydride, or tetrafluoroborate.

2. The method of claim 1 wherein the activating co-catalyst is selected from the group consisting of alkylalumoxanes, mixtures of alkyl alumoxanes with one or more trialkyl aluminum or trialkyl boron compounds, and mixtures of alkylalumoxanes with aluminum halides or boron halides and an alkylating agent.

3. The method of claim 2 wherein A is —CH($R^4$)—; $R^3$ is alkyl; and X is chlorine.

4. The method of claim 3 wherein $R^1$ and $R^2$ are hydrogen.

5. The method of claim 3 wherein $R^1$ and $R^2$ are methyl.

6. The method of claim 4 or 5 wherein $R^3$ is a $C_4$ alkyl and $R^4$ is a $C_4$ hydrocarbyl.

7. The method of claim 2 wherein $R^1$ and $R^2$ are hydrogen; $R^3$ is alkyl; A is —$CY_2CY_2$—; and X is chlorine.

8. The method of claim 7 wherein $R^3$ is a $C_4$ alkyl and A is —$CF_2CF_2$—.

* * * * *